US012667089B2

(12) United States Patent
Dong et al.

(10) Patent No.: US 12,667,089 B2
(45) Date of Patent: Jun. 30, 2026

(54) BREEDING METHOD OF NEW VARIETY OF HARD-SHELLED RAZOR CLAMS

(71) Applicant: Zhejiang Wanli University, Ningbo City (CN)

(72) Inventors: Yinghui Dong, Ningbo City (CN); Hongqiang Xu, Ningbo City (CN); Tianbao Mo, Ningbo City (CN); Hanhan Yao, Ningbo City (CN); Lin He, Ningbo City (CN); Jing He, Ningbo City (CN); Zhihua Lin, Ningbo City (CN)

(73) Assignee: Zhejiang Wanli University, Ningbo City (CN)

( * ) Notice: Subject to any disclaimer, the term of this patent is extended or adjusted under 35 U.S.C. 154(b) by 631 days.

(21) Appl. No.: 18/122,149

(22) Filed: Mar. 16, 2023

(65) Prior Publication Data

US 2023/0292722 A1      Sep. 21, 2023

(30) Foreign Application Priority Data

Mar. 17, 2022    (CN) .......................... 202210263655.2

(51) Int. Cl.
*A01K 67/62*            (2025.01)
(52) U.S. Cl.
CPC .................................... *A01K 67/62* (2025.01)
(58) Field of Classification Search
CPC ................................ A01K 67/00; A01K 67/62
See application file for complete search history.

(56) References Cited

U.S. PATENT DOCUMENTS 4,170,197 A * 10/1979 Walker ................... A01K 61/54
119/240

FOREIGN PATENT DOCUMENTS

| CN | 108012964 A * | 5/2018 | ............. A01K 61/54 |
| CN | 108040938 B * | 4/2020 | ............. A01K 61/54 |
| CN | 113951191 A * | 1/2022 | ............. A01K 67/62 |
| CN | 114158499 A * | 3/2022 | ............. A01K 61/54 |
| CN | 114158500 A * | 3/2022 | ............. A01K 61/54 |
| WO | WO-2004068941 A1 * | 8/2004 | ............. A01K 61/60 |
| WO | WO-2019135055 A1 * | 7/2019 | ............. A01K 61/56 |

OTHER PUBLICATIONS

Machine Translation of CN-108012964-A, Yu, Rui-hai, May 11, 2018 (Year: 2018).*
Machine Translation of CN-108040938-B, Zhang, Yue-huan, Apr. 3, 2020 (Year: 2020).*
Machine Translation of CN-113951191-A, Wu, Si-yuan, Jan. 21, 2022 (Year: 2022).*
Machine Translation of CN-114158499-A, Qin, Yan-ping, Mar. 11, 2022 (Year: 2022).*
Machine Translation of CN-114158500-A, Qin, Yan-ping, Mar. 11, 2022 (Year: 2022).*
Machine Translation of WO-2019135055-A1, Galavielle Pierre-Henri, Mar. 11, 2022 (Year: 2019).*

* cited by examiner

*Primary Examiner* — Kimberly S Berona
*Assistant Examiner* — Katherine June Walter
(74) *Attorney, Agent, or Firm* — Getech Law LLC; Jun Ye

(57) ABSTRACT

The present invention provides a breeding method of a new variety of hard-shelled razor clams, comprising the following steps: a. Estimating the heritability of shell hardness trait: constructing full-sib families to estimate the heritability of the growth and shell hardness traits of the razor clams; b. Selecting individuals with hard shells from basic population using an electronic hardness tester of material mechanics as the broodstock clams; c. Artificially-induced spawning; d. The offspring grow-out; e. Purification of the new strain: with the new strain of hard-shelled generation 1 adults obtained in step d as broodstocks, repeating the steps c and d several times to obtain a new variety of razor clams with hard shells, and the shell hardness trait of razor clams has stable heritability.

6 Claims, No Drawings

BREEDING METHOD OF NEW VARIETY OF HARD-SHELLED RAZOR CLAMS

This application is based upon and claims priority to Chinese Patent Application No. 202210263655.2, filed on Mar. 17, 2022, the entire contents of which are incorporated herein by reference.

TECHNICAL FIELD

The present invention relates to the genetic breeding of aquatic animal, and in particular to construction and application of a breeding method of a new variety of hard-shelled razor clams.

BACKGROUND

Razor clams belong to Veneroida, Lamellibranchia, Mollusca. The commercially-cultured species comprise *Sinonovacula constricta, Solen grandis, Solen strictus, Cullellum scalprum*, and *Sinonovacula rivularis* and the like, which have been healthy food with good taste, high-protein and low-fat in meat, and the meat yield is about 60%, contribute to the high nutrition and economic values of razor clams. In recent years, the culture industry of razor clams represented by *S. constricta* continuously development rapidly with an annual production of more than 850,000 tons. However, a few researches about excellent varieties of razor clams were documented. At present, the breeding goal is mainly focus on fast-growing and stress-resistance varieties. No varieties of razor clams with improved quality are reported.

Compared with most bivalve species such as oysters, mussels, clams and blood clams, the razor clams have a thin and fragile shell with an average thickness of only 0.67 mm, which is ⅓ to ⅕ of that of common bivalves. The shells of razor clam are semi-closed and extremely susceptible to attack of predators or bioturbation of other living organisms. During the larvae or the spat stage, the thin and fragile shells often lead to higher requirements for intermediate breeding technologies such as seed washing, separation and seeding, and bringing large losses. During the clam growth-out stage, harvesting and transportation bring different degrees of damages to the species (close to 10%), increasing more deaths and reducing the market value, and finally bringing huge losses to the razor clam industry. Furthermore, the thin and fragile shells of the razor clams are unfavorable for the development of mechanized harvesting, restricting the efficient and sustainable development of the industry. Therefore, a new variety with high shell hardness and high stress resistance is of significance for upgrade and sustainable development of the razor clam's industry. The early research of the investor reveals that the shell hardness trait of the razor clams is a quantitative trait, which has weak genetic correlation with the growth traits. Further, the genetics analysis reveals that the trait has medium heritability. The result provides scientific basis for research of the invention.

SUMMARY

In order to solve the problems of harvesting and transportation resulting from the thin and fragile shells of razor clams, the present invention provides a breeding method of a new hard-shelled razor clams variety. The technology could fundamentally relieve the problem of high breakage rate arising from harvesting and transportation of razor clams, which would contribute to increasing the production, and promoting the fast and sustainable development of the razor clam industry.

In China, most economic mollusks such as oysters, scallops, short-necked clams, and mussels have hard and completely-closed double shells to protect their soft tissues. The razor clams are extremely susceptible to external physical damage due to the thin and fragile shell, leading to deaths and causing indirect production reduction and lower benefits. Therefore, the main inventive point of the invention is to breed a new variety of razor clams with hard shells.

The present invention provides a breeding method of a new variety of hard-shelled razor clams, which comprises the following steps:

a. Estimating heritability of shell hardness trait: constructing full-sib families to estimate the heritability of the growth trait and shell hardness trait of the razor clams;

b. Selecting individuals with hard shells from basic population using an electronic hardness tester of material mechanics as the broodstocks;

c. Artificially-induced spawning: the breeding population is obtained in step b, washing and sterilizing the clams and then placing them in a well-ventilated position free from sunshine for drying for 2 to 4 hours in the evening, and combining injection of 5-hydroxytryptamine via foot with flowing water stimulation to perform artificially-induced spawning;

d. The offspring grow-out: the clams obtained in step c as reproduction population, the rearing of larvae, spat, adults followed routine bivalve culture procedures to obtain new strain of razor clams (Generation 1, G1) with high shell hardness;

e. Strain purification: with the new strain of hard-shelled G1 adults obtained in step d as broodstocks, repeating the steps c and d several times to obtain a new variety of hard-shelled razor clams with, and the shell hardness trait has stable heritability through several generations of consecutive purification. Particularly, the heritability evaluation in step a is to construct half-sib families using the nested design method, breeding values and heritability for the traits (shell height, shell length, shell width, total weight and shell hardness) of the new variety of hard-shelled razor clams were calculated.

Particularly, the electronic hardness tester in step b is a mechanical apparatus optimized and applied by the inventor to perform accurate measurement for the shell hardness trait of the razor clams. The specific step is to select 200 individuals and measure the shell hardness using the electronic hardness tester, sort the hardness values and determine a constant stress value for the breeding population. The test mode of the electronic hardness tester is modified so that the constant stress value is used to perform parent screening. Finally, crushed individuals were eliminated and individuals with high shell hardness were retained as the broodstocks.

Particularly, the step c of injecting 5-hydroxytryptamine is to randomly select 50-100 individuals from the broodstocks and inject 0.1 to 0.2 ml 5-hydroxytryptamine with 0.02 to 0.04 mmol/L to the feet of the razor clams.

Particularly, in the step e of strain purification process, the several times of repeating the process are preferably 3 to 4 times and the several generations are preferably 2 to 3 generations.

In the present invention, a new variety of hard-shelled razor clams is obtained by the process of heritability evaluation, broodstocks screening, artificially-induced spawning and strain purification. The new variety of hard-shelled razor clams obtained by the present invention has high shell hardness and strong transportation resistance as well as growth advantage, and the shell hardness trait of the razor families have average shell hardness, shell length, shell width, shell height and wet weight increased by 15.2%, 12.1%, 10.1%, 8.5% and 44.7%, respectively.

TABLE 1

Comparison of shell hardness and growth traits between hard-shelled families and control families in *S. constricta* at the 10-month-old

| Traits | Heritability | Hard-shelled families | | | Control families | | |
| | | Average value | Standard difference | Variation coefficient | Average value | Standard difference | Variation coefficient |
|---|---|---|---|---|---|---|---|
| Shell hardness | 0.32 ± 0.16 | 19.62 | 4.40 | 22.43 | 17.03 | 3.55 | 20.85 |
| Shell length | 0.50 ± 0.15 | 54.07 | 3.17 | 5.86 | 48.22 | 0.97 | 2.01 |
| Shell height | 0.36 ± 0.13 | 17.84 | 1.34 | 7.51 | 16.20 | 0.75 | 4.63 |
| Shell width | 0.56 ± 0.12 | 12.79 | 1.07 | 8.37 | 11.79 | 1.07 | 9.08 |
| Shell weight | 0.60 ± 0.16 | 10.13 | 1.90 | 18.76 | 7.00 | 1.09 | 15.57 | clams has stable heritability. It has been proven that there is a promising market for the new variety.

EMBODIMENTS

The technical solutions of the present invention will be further described by referring to the specific embodiments to make these technical solutions clearer and more understandable. Unless otherwise stated, the raw materials used in the embodiments of the present invention are materials commonly used in the field and the methods used in the embodiments are also conventional methods of the field.

1. Family Construction and Heritability Evaluation of the Shell Hardness Trait a. Broodstocks screening: on Oct. 1, 2018, a cultured population of *S. constricta* was collected in Changjie town, Ningbo city, China. The razor clams with shell length of about 6 cm were selected. 100 razor clams with high shell hardness were screened out by using the electronic hardness tester with a pressure of 22 N·mm.

b. Family construction: After injecting of 5-hydroxytryptamine (0.04 mM) via feet and flowing water stimulation, the individuals were placed into a beaker with a water temperature 20-26° C. and salinity 12-15 ppt for the single spawning induction. 36 hard-shelled full-sib families (comprising 12 half-sib families) were constructed using the method of nested design, while three control group families were constructed.

c. Larva culture and grow-out: The processes of fertilization and incubation, larva culture, spats nursery and pond culture may be referred to the conventional larvae or spat culture management method; during the entire life cycle, the clam density of each family is consistent to prevent cross contamination. Finally, 27 full-sib families (comprising 9 half-sib families) and 3 control group families were left.

d. Heritability evaluation: The individual animal model of the ASReml 3.0 software was used to perform variance analysis on the shell hardness traits of the 27 full-sib families at the 10-month-old, the moderate heritability (0.32±0.16) of the shell hardness trait was observed in *S. constricta*, which implied the genetic improvement for shell hardness can be carried out by selection breeding method. The data of the shell hardness and the growth-related traits is shown in Table 1. Compared with the control groups, the hard-shelled 2. Breeding of a New Strain of Hard-Shelled *S. constricta* a. Broodstock screening: On Aug. 20, 2019, a wild population of *S. constricta* was collected in a coastal intertidal zone of Changjie town (29.19° N, 121.77° E), Ningbo city, China. 70 kg of 1-year-old razor clams with the shell length of about 6 cm were selected, and the shell hardness of 200 individuals were measured by the electronic hardness tester to establish a normal distribution diagram of the trait. Then the broodstocks were screened with constant pressure value of 24 N·mm and a selection intensity of 20%. Finally, a total of 1,120 individuals were retained comprised the G0 broodstock after remove individuals with poor activity.

b. Maturity acceleration of broodstocks: The disinfected sea mud of the intertidal zone was spread in an indoor cement pond to form a thickness of about 8 cm. 1,120 razor clams obtained in step a were spread uniformly in the pond with water changed one to two times a day. Dead individuals were removed daily. Artificial microalgae *Chaetoceros muelleri, Phaeodactylum tricornutum* and *Tetraselmis* sp. were provided for the nutrition enhancement to improve the spawning rate of the wild clams. After enhanced cultivation of 20 d, the gonads of the 1,120 clams were matured.

c. Offspring grow-out: The 1000 razor clams obtained in the step b comprised the breeding population, spawning induction was performed by combination of injection of 5-hydroxytryptamine (0.04 mM) via feet and flowing water stimulation. After fertilization and incubation, larva cultivation, intermediate rearing and pond culture, a new strain of hard-shelled *S. constricta* (G1) was obtained.

d. The strain purification: The steps b to c were repeated to generate the second generation (G2) using the G1 adults as broodstocks on Aug. 25, 2020. Through two consecutive generations of purification, a new strain of *S. constricta* with hard-shells was obtained. In September of 2020 and 2021, 100 12-month-old razor clams of G1 and G2 were randomly sampled to detect genetic progress, and the shell hardness and growth data were shown in Table 2. After purification of two consecutive generations, the shell hardness trait of *S. constricta* strain was increased by 30.8% and the growth trait was increased by above 10%, indicating obvious effect of genetic improvement.

In conclusion, by selecting individuals with high shell hardness of two consecutive generations, a new *S. constricta* strain with high shell hardness and fast growth traits which is suitable for commercial production is obtained, the work providing important materials for higher production, quality improvement and industrial upgrade of *S. constricta*.

TABLE 2

| | Comparison of shell hardness and growth traits in the strain of hard-shelled *S. constricta* | | | | | |
| --- | --- | --- | --- | --- | --- | --- |
| Generations | Shell hardness (N) | Shell length (mm) | Shell width (mm) | Shell height (mm) | Wet weight (g) | Shell weight (g) |
| G0 | 22.16 ± 4.87 | 56.01 ± 4.44 | 18.25 ± 1.14 | 12.22 ± 1.28 | 11.33 ± 2.02 | 2.01 ± 0.38 |
| G1 | 24.73 ± 5.44 | 58.61 ± 4.36 | 19.00 ± 1.50 | 13.89 ± 1.20 | 11.68 ± 2.69 | 2.32 ± 0.28 |
| G2 | 29.21 ± 3.07 | 62.33 ± 4.05 | 20.87 ± 1.29 | 14.03 ± 1.02 | 12.82 ± 2.67 | 2.72 ± 0.25 |

The invention claimed is:

1. A method for breeding a hard-shelled razor clam strain, comprising:

a step (a) comprising:

constructing a plurality of full-sib families of razor clams using a control population of razor clams;

measuring a growth trait and a shell hardness trait for the plurality of full-sib families to obtain a measured result of the growth trait and the shell hardness trait; and performing a heritability evaluation based on the measured result to obtain a heritability evaluation result;

a step (b) comprising:

during a reproductive season of the razor clams, collecting razor clam individuals from a predetermined sea area to form a base population;

measuring shell hardness of each razor clam individual in the base population using an electronic hardness tester for material mechanics; and selecting, from the base population, the razor clam individuals having measured shell hardness greater than a predetermined selection threshold as a breeding population;

a step (c) comprising:

washing and sterilizing the breeding population, and then air-drying the breeding population in a ventilated shaded place for 2 to 4 hours; and inducing spawning of the breeding population by injecting 5-hydroxytryptamine into feet of the breeding population in combination with running-water stimulation to obtain offsprings of the breeding population;

a step (d) comprising:

growing out the offsprings to obtain target individuals of a first-generation hard-shell razor clam strain based on the heritability evaluation result; and a step (e) comprising:

using target individuals of the first-generation hard-shell razor clam strain as the breeding population, repeating the steps (c) and (d) for 3 to 4 rounds to obtain one or more generations of hard-shell razor clam strains.

2. The method for breeding of a hard-shelled razor clam strain of claim 1, wherein the plurality of full-sib families of razor clams is constructed using a nested design method, and the growth trait comprises a shell height, a shell length, a shell width, and a total weight.

3. The method for breeding of a hard-shelled razor clam strain of claim 1, wherein the electronic hardness tester is a mechanical apparatus optimized and applied to perform accurate measurement for the shell hardness trait of the razor clams; and the step (b) further comprises:

selecting 200 razor clam individuals;

measuring the shell hardness of the 200 razor clam individuals using the electronic hardness tester, and sorting the measured hardness values;

determining a constant-pressure value for the breeding population;

configuring the electronic hardness tester to perform parent screening by testing the 200 razor clam individuals using the constant-pressure value; and eliminating crushed individuals and retaining individuals having shell hardness greater than the constant-pressure value as the breeding population.

4. The method for breeding of a hard-shelled razor clam strain of claim 1, wherein the step (c) further comprises:

randomly selecting 50-100 individuals from the breeding population; and injecting, using a syringe, 0.1 to 0.2 ml of 5-hydroxytryptamine with 0.02 to 0.04 mmol/L to the foot of each razor clam.

5. The method for breeding of a hard-shelled razor clam strain of claim 1, wherein in the step (e), the one or more generations of hard-shell razor clam strains includes two or three generations hard-shell razor clam strains.

6. The method for breeding of a hard-shelled razor clam strain of claim 1, wherein the step (c) further comprises:

randomly selecting 50-100 individuals from the breeding population;

injecting, using a syringe, 0.1 to 0.2 ml of 5-hydroxytryptamine with 0.02 to 0.04 mmol/L to the foot of each razor clam; and using 0.05 mmol/L EDTA solution as a stimulating substance for the running-water stimulation.

* * * * *